United States Patent [19]

Wieting et al.

[11] Patent Number: 5,035,709
[45] Date of Patent: Jul. 30, 1991

[54] MECHANICAL HEART VALVE WITH COMPLIANT SEWING RING

[75] Inventors: David W. Wieting, Irvine; Than Nguyen, Huntington Beach; Robert Stobie, Mission Viejo; Hung L. Lam, Norco; Ralph Kafesjian, Costa Mesa, all of Calif.

[73] Assignee: Baxter International Inc., Deerfield, Ill.

[21] Appl. No.: 502,158

[22] Filed: Mar. 29, 1990

[51] Int. Cl.$^5$ .............................................. A61F 2/24
[52] U.S. Cl. .......................................................... 623/2
[58] Field of Search ............................................. 623/2

[56] References Cited

U.S. PATENT DOCUMENTS

| | | |
|---|---|---|
| 3,365,728 | 1/1968 | Edwards et al. ...................... 623/2 |
| 3,509,582 | 5/1970 | Pierie et al. ............................ 623/2 |
| 3,534,410 | 10/1970 | Raible .................................... 623/2 |
| 3,723,996 | 4/1973 | Raible et al. ........................... 623/2 |
| 4,078,268 | 3/1978 | Possis .................................... 623/2 |
| 4,254,508 | 3/1981 | Bokros .................................. 623/2 |
| 4,276,658 | 7/1981 | Hanson et al. ........................ 623/2 |
| 4,443,894 | 4/1984 | Klawitter .............................. 623/2 |
| 4,535,483 | 8/1985 | Klawitter et al. .................... 623/2 |
| 4,680,031 | 7/1987 | Alonso .................................. 623/2 |

Primary Examiner—Ronald Frinks
Attorney, Agent, or Firm—Michael C. Schiffer

[57] ABSTRACT

A mechanical heart valve having one or more leaflets pivotally fitted in a substantially cylindrical shaped valve body formed from a resiliently deformable material. A stiffening member formed from substantially nonresilient material fit about the valve body exterior wall to provide structural integrity to the valve body. Stresses which are normally applied to the heart valve body during the opening and closing of the valve are absorbed or cushioned by the incorporation of a rubber-like body between the stiffening member and the retainer member. Further cushioning is provided by incorporating another rubber-like body in the sewing ring. This second body extends out from the exterior surface of the valve body. Finally, a length of fabric is positioned about the retainer and shock absorbing bodies. This design provides a precisely calibrated rotational torque which allows for optimum orientation of the leaflets by the implanting surgeon.

10 Claims, 2 Drawing Sheets

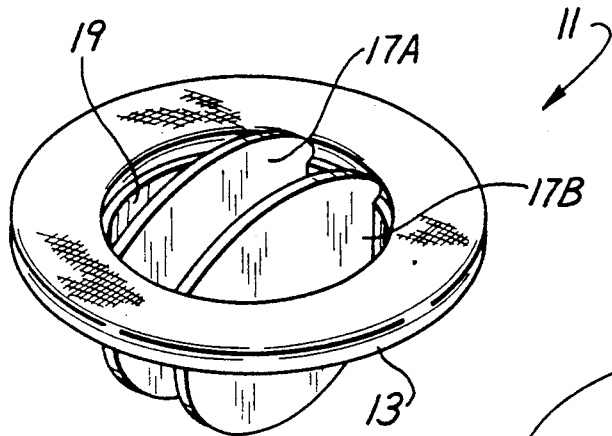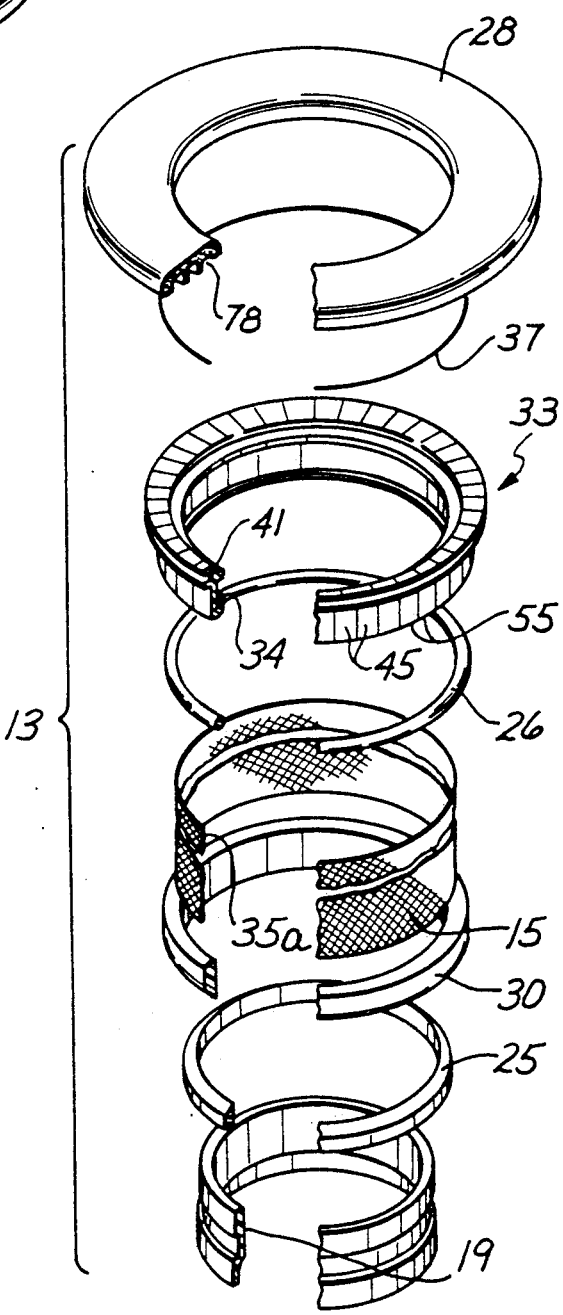

MECHANICAL HEART VALVE WITH COMPLIANT SEWING RING

BACKGROUND OF THE INVENTION

The present invention is directed to heart valves, and specifically to mechanical heart valves. The present invention has particular applicability to bileaflet mechanical heart valves of the type disclosed in U.S. Pat. No. 4,535,483, issued to Klawitter et al on Aug. 20, 1985.

Heart valves are generally of two different types, biological and mechanical. Both offer advantages and disadvantages that are well known to those skilled in the art. One major concern with both types of heart valves is the wearing of critical components during the normal opening and closing of the valve. Mechanical heart valves experience wear from the opening and closing movement of the occluders. Further, the impact of the occluders against the valve body results in stress to the valve. Mechanical heart valves have also shown increased levels of hemolysis over tissue valves. However, due to the long term durability of mechanical hearts attempts have been made to reduce closing forces and associated stress and hemolysis.

Heart valves have been designed to reduce normal wear, and minimize the effects of the impact of the occluders against the valve body. For example, U.S. Pat. No. 4,443,894, issued to Klawitter on Apr. 24, 1984, discloses a heart valve having two occluders. Each occluder is formed with guides or protrusions which fit dog shaped depressions at opposite sides of the valve body. The occluders not only experience pivoting movement during the opening and closing of the heart valve, but experience a translation movement. The combination of the pivoting and translation movement of the occluder unloads strain applied to the occluder guides.

Other heart valve designs cushion the impact of the opening and closing of the valve by incorporating a rubber or silicone material in the valve sewing ring. The use of the rubber or silicone material in many of these heart valve designs was intended to provide a more compliant material for conforming to irregular tissue annuli, with the cushioning effect being accidental. For example ball poppet mechanical heart valves disclosed in U.S. Pat. No. 3,365,728, issued to Edwards et al on Jan. 30, 1968, U.S. Pat. No. 3,509,582, issued to Pierie et al on May 5, 1970, U.S. Pat. No. 3,534,410, issued to Raible on Oct. 20, 1970, and U.S. Pat. No. 3,723,996, issued to Raible et al on Apr. 3, 1973, provide for silicone rubber in the sewing ring. A tissue valve incorporating an elastic member in the sewing ring is disclosed in U.S. Pat. No. 4,680,031, issued to Alonso on July 14, 1987.

One particular type of mechanical heart valve is generally referred to as a bileaflet mechanical valve. This type of heart valve has demonstrated superior blood flow and a reduction in thromboembologic complications and blood hemolysis. One cause for the reduction of blood hemolysis is the use of pyrolytic carbon in forming the blood contacting portions of the heart valve. Pyrolytic carbon is blood compatible. However, pyrolytic carbon is a deformable, inelastic material which provides limited structural rigidity. An example of a pyrolytic carbon coated mechanical bileaflet heart valve is manufactured by St. Jude Medical, Inc. of Minneapolis, Minn. and disclosed under U.S. Pat. No. 4,078,268 issued to Possis and 4,276,658 issued to Hanson et al.

Some workers have suggested providing structural rigidity to the pyrolytic carbon heart valve body. One approach to providing this structural rigidity has been to incorporate a stiffener ring 25 about the pyrolytic carbon heart valve body to provide structural support. See U.S. Pat. No. 4,535,483, issued to Klawitter et al. The stiffening ring is situated about the exterior surface of the heart valve body in close proximity to the retainer ring of the sewing ring. The retainer function to maintain the sewing ring about the heart valve body. The disclosed heart valve design also incorporates a "resilient polymeric filler ring 76". formed of low density or foam polytetrafluoroethylene in the sewing ring.

The Klawitter et al bileaflet heart valves provide for the advantages of bileaflet heart valves while also providing structural rigidity through the use of the stiffening ring. The use of the "filler ring 76", which has primarily been utilized in heart valves positioned at the mitral valve location provides a degree of cushioning of the impact of the occluders against the valve body during closing.

While the Klawitter et al heart valves provide numerous advantages over previously available heart valves, both mechanical and tissue. recent investigations have shown the continued presence of the stress effects associated with the opening and closing of the valve occluders. It would thus be desirable to provide for a modification of bileaflet heart valves having a pyrolytic carbon valve body incorporating a stiffening ring which further reduces the stress effects from the opening and closing of the valve occluders.

SUMMARY OF THE INVENTION

The present invention is directed at a mechanical heart valve having a substantially cylindrical shaped valve body surrounded by a sewing ring which is formed from an inelastic, deformable material. The valve includes one or two leaflets which are pivotally mounted to an interior wall to pivot within an opening formed through the cylindrical valve body. The valve further includes one or more stops which are engaged by the occluders to prevent further movement. The stops lie along the interior wall of the valve body.

As stated, the valves of the invention are of the type which incorporate a stiffening member formed from substantially nonresilient material fitted about the valve body exterior wall. This stiffening member provides structural integrity to the valve body.

The cushioning of the stresses applied to the heart valve during the opening and closing of the valve is incorporated into the sewing ring. The sewing ring is positioned about the valve body and includes a rigid retainer that is formed to be held about the valve body exterior surface. The construction of the retainer ensures that the sewing ring will remain positioned about the valve body. A shock absorbing body is disposed in the sewing ring between said stiffening member and said retainer. This shock absorbing body is constructed from a rubber-like material to absorb and cushion the impact from the closing occluders engaging the stops.

Further cushioning is provided by incorporating another rubber-like body in the sewing ring. This second body extends out from the exterior surface of the valve body. Finally, a length of fabric is positioned about the retainer and shock absorbing bodies.

DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a prospective view of a bileaflet mechanical heart valve in accordance with an embodiment of the invention;

FIG. 2 is an exploded view of the mechanical heart valve of FIG. 1;

DESCRIPTION OF THE PREFERRED EMBODIMENTS

Figure 4:
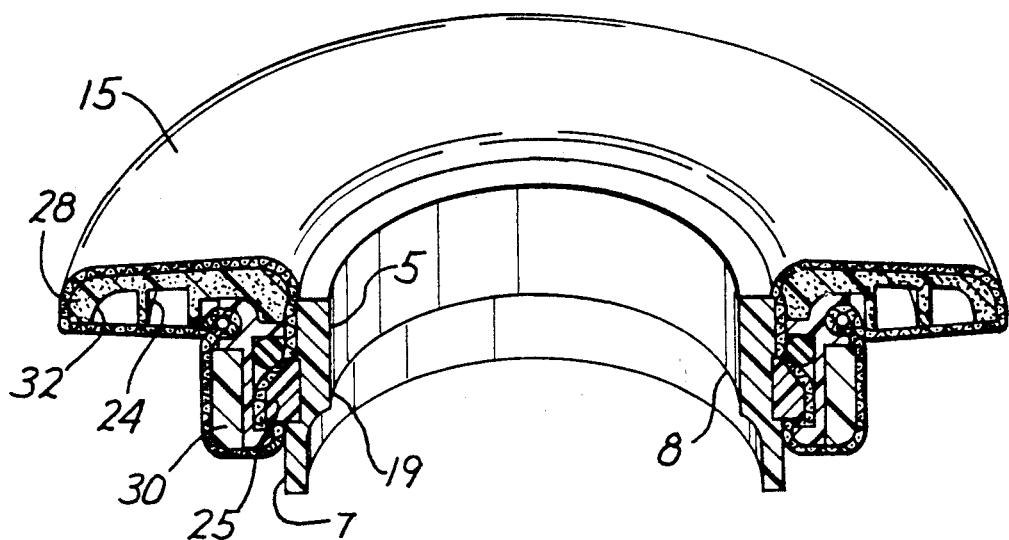
FIGS. 3 and 4 are different cross-sectional views of the sewing ring and valve body of the mechanical heart valve of FIG. 1.

The present invention involves the incorporation of cushioning means into the sewing ring of a heart valve, and particularly a mechanical heart valve having a valve body formed from inelastic deformable material, and specifically pyrolytic carbon. As will be described more fully herein, the valve leaflets are pivotally mounted in the valve body orifice, and specifically, pivot pegs or protrusions on the leaflets are fitted in depressions formed along the inside surface of the valve body. The benefit of using this type of material allows for the deformation of the valve body to position the leaflets inside the valve orifice.

The invention has particular applicability to the heart valves disclosed in the previously discussed U.S. Pat. Nos. 4,254,508 and 4,535,483, all of which are incorporated herein with respect to the description of the heart valve and manner of constructing the same. As is known from these prior patents, the material used to construct the heart valve body is of the type which possesses little, if any, structural support. The heart valve is provided with structural support by the placement of a stiffener ring about the heart valve body. As also disclosed in these prior patents, a retainer ring is incorporated into the sewing ring for the purpose of mounting the sewing ring about the valve body.

Previously designed heart valves incorporate an elastic member in the sewing ring. This elastic member typically extends outward from the valve body to form a bulge in the sewing ring through which sutures are pushed during the implantation of the valve. See in particular the valve disclosed in incorporated U.S. Pat. Nos. 4,254,508 and 4,535,483. This elastic member also functioned to cushion the stress affects caused by the opening and closing of the valve leaflets. It has now been discovered that additional cushioning at the point between the stiffening and retainer rings further enhances the durability of the resulting heart valve. Accordingly, the heart valve of the invention incorporates a cushion member at a location between the stiffening and retainer rings.

The invention will now be described in greater detail with reference to the several figures. Illustrated in these several Figures is a heart valve 11 which carries a suture ring assembly 13. The suture ring assembly 13 has an outer fabric covering 15 of porous fabric which can be sutured to the tissue of the heart and to which the fibrous tissues of the heart will attach during healing.

The illustrated heart valve 11 has a pair of generally semi-circular leaflets 17A and B which are mounted within an orifice ring or valve body 19 for pivoting between an open position to allow blood flow through the orifice or passageway and a closed position to block blood flow. The leaflets 17A and B are mounted in the orifice ring 19 by suitable interengagement means (not shown) which may include depressions and/or protuberances on the interior of the orifice ring 19 and cooperating depressions and/or protuberances at the periphery of each leaflet, which interengagement means forms no part of the present invention.

The valve body 19 is substantially cylindrical in shape with interior and exterior walls, as seen respectively in FIG. 4 at 5 and 7. The interior wall 5 defines a substantially circular first opening through the valve body 19. Interior wall 5 further includes an annular ledge 8. The occluders or leaflets 17A and 17B are dimensioned to engage the annular ledge 8 when in their closed position, with the annular ledge 8 restricting further pivoting action of the leaflets 17A and 17B.

The orifice ring 19 is formed of an inelastic deformable material in order to be deformed for insertion of the valve members 17. When the orifice ring 19 returns to its annular configuration, the depressions and/or protrusions of the orifice ring 19 and valve members 17 mount the valve members 17 for pivotal motion. A particularly suitable material for formation of valve members 17 and orifice rings 19 is pyrolytic carbon or pyrocarbon, such as that sold under the name PYROLITE ™ registered trademark of Carbomedics, Inc., Austin, Tex. which has a surface with highly thromboresistant characteristics. Orifice ring 19 formed of completely or partially of pyrolytic carbon or pyrocarbon may be deformed sufficiently for mounting of the valve members 17.

Orifice ring 19 requires stiffness in order to minimize deformation during the implantation procedure. This is accomplished by fitting a member, typically a ring shaped member, of a nondeformable stiff material about the orifice ring 19. In the illustrated embodiment, the orifice ring 19 is formed with a shallow outwardly facing annular groove 23. This groove 23 is dimensioned to receive a stiffener ring 25, which interfits with the annular groove and stiffens the orifice ring 19 against deformation during surgical implantation. This stiffener ring 25 will also serve as a point of attachment for the sewing ring assembly. The stiffener ring 25 is held in interference fit within the shallow annular groove 23, and is of a thickness to extend radially outward from the orifice ring 19.

The sewing ring assembly includes an outer surrounding retainer ring 33 and a fabric covering 15 which is suturable to the tissues of the heart. The retainer ring 33 has an interior region or groove 34 which accommodates the outwardly protruding portion of the stiffener ring 25. The retainer ring 33 includes a central rigid annulus 43 from which extends a circular section 41. The circular section 41 is formed with numerous slits. These slits provide the circular section 41 with a degree of deformability. A portion of the fabric covering 15 is interposed and held between the stiffener ring 25 and the retainer ring 33.

Figure 3:
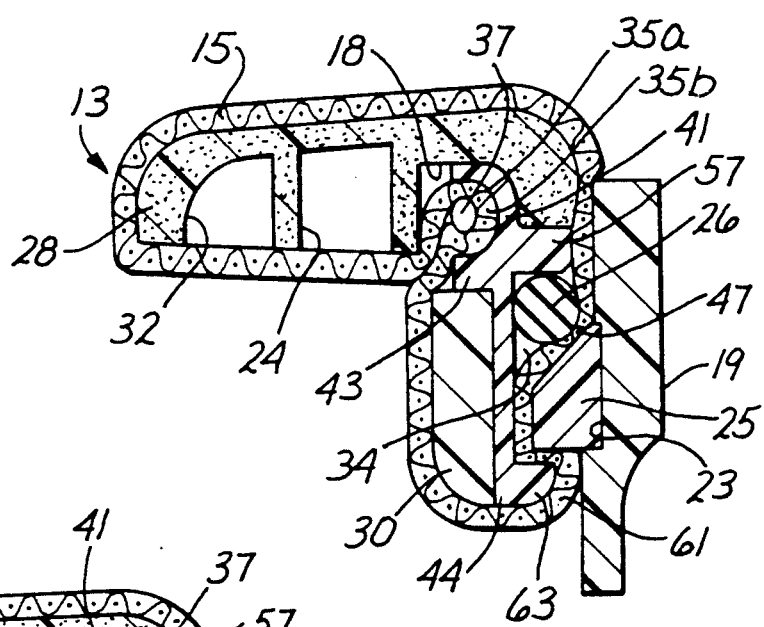

The sewing ring assembly 13 further includes a shock absorbing member 26 interdisposed between the stiffener ring 25 and the retainer ring 33, and a cushioning member 28 disposed to extend outwards from the orifice ring 19. The sewing ring assembly 13 may also include a spacer 30, as seen in FIGS. 3 and 4, when the heart valve 11 is of a larger dimension, i.e. thirty-one to thirty-three millimeters in diameter. As further seen in FIG. 3, the cushioning member 28 is provided with two annular grooves, seen at 32 and 24. These grooves 32 and 24 increase the flexibility of the sewing ring, further cushioning the impact and stress of the opening and closing leaflets 17.

The fabric covering 15 is generally of a tubular shape, as best seen in the exploded view of the sewing ring in FIG. 2. The tubular shaped fabric covering 15 is wrapped about the retainer ring 33, cushioning member 28, shock absorbing member 26, and if present, spacer 30. The ends 35a and 35b of the fabric covering 15 are then joined together to fully surround the retainer ring 33, cushioning member 28 and shock absorbing member 26. The junction between the overlapping ends 35a and b are positioned in the circular section 41, as seen in FIG. 3. The construction of the sewing ring assembly 13 is performed as follows. First the stiffener ring 25, which is formed of metal, is shrink-fitted about the orifice ring 19 to form an interference fit within the outwardly facing groove 23 by first heating it to expand its diameter. The fabric covering 15 is wrapped into its closed loop configuration around the retainer ring 33, shock absorbing member 26 and cushioning member 28. The fabric member ends 35a and 35b are joined with a suture, seen at 37, which is snugly fitted into the circular section 41. The fabric covered retainer ring 33, is thereafter snapped onto the protruding portion of the stiffener ring 25 by means of a deformable segment consisting of a ring of resilient prongs or tangs 45 that extend from the annulus 43 in the opposite direction from the circular section 41.

The sewing ring assembly 13 will now be described in greater detail. The stiffener ring 25 is of annular shape having a generally rectangular cross section; however, the upper outer edge 47 is chamfered. This chamfered edge 47 provides a spatial area between the stiffener ring 25 and retainer ring 33 for receiving the shock absorbing member 26, as best seen in FIG. 3. The chamfered edge 47 also assists in the snapping engagement by the retainer ring 33 as described herein below. The stiffener ring 25 is dimensioned to snugly fit within the shallow groove 23 of the orifice ring 19. The thickness of the stiffener ring is greater than the depth of the groove 23 to insure that a portion extends radially outward. This provides the portion upon which the retainer ring 33 is snapped onto.

As stated, the stiffener ring 25 is heated to high temperatures until it expands sufficiently to slide over the orifice ring 19. The heat-expanded stiffener ring 26 is positioned around the groove and snuggly seated therein by cooling to ambient temperatures. The stiffener ring 25 is formed from a metal material having a sufficient coefficient of thermal expansion to permit ample expansion to fit around the orifice ring 19. Although the stiffener ring 25 in the final assembly is shielded by the fabric covering 15 from contact with blood or tissue, the metal used to form the stiffener ring 25 is preferably biocompatible and thromboresistant. A Co-Cr alloy is a preferred material for formation of the stiffener ring which may be heated to about 900° F. for placement about the orifice ring 19.

The retainer ring 33 is fabricated as a unitary, generally tubular piece of metal appropriately slit to provide the rings of tines 41 and tangs 45 extending in opposite directions from the central annulus 43. Although the retainer ring 33 is fully covered with fabric in the complete sewing ring assembly 13, the metal is also selected for biocompatibility and thromboresistance. The central annulus 43 is of a thickness sufficient to resist deformation under normal conditions found during assembly of the sewing ring assembly 13. The tangs 45 are less thick to allow for deflection, but should be sufficiently thick to provide a degree of "memory" to allow the tangs to return to their original configuration. The circular section 41 is sufficiently large to snugly receive the sutured ends 35A and 35B of the fabric covering 15. A preferred metal for fabrication of the retainer ring 33 is titanium. Other metals, such as stainless steel, may also be used to fabricate the retainer ring 33, or a material having similar deformable properties might be used instead of metal.

The inner surface of the retainer ring 33, which will face the orifice ring 19, is formed at a location adjacent the central annulus 43 with an inwardly facing annular groove 34. This annular groove 34 is dimensioned to snugly fit the protruding portion of the stiffener ring 25. As seen in FIG. 3, the annular groove 34 defines a lower annular rim 44 at one end of the retainer ring 33 and an opposite upper surface or overhang 57. The rim 44 and overhang 57 are spatially separated sufficiently to receive the protruding portion of the stiffener ring 25. The groove 34 is also proportioned to accommodate a single layer of the fabric covering 15. This allows the retainer ring 33 to snap upon the stiffener ring 25 having a layer of the fabric covering 15 disposed thereon.

The formation of the tangs 45 promotes the ease in snapping the retainer ring 33 about the stiffener ring 25. As seen, the lower portion containing the annular groove 34 is formed with a plurality of slits 55 which extends from the central annulus 43 to the lower rim 44, as best seen in FIG. 2. This defines the ring of resilient tangs 45. The slits 55 divide the lower rim 44 into radially inwardly extending lugs 61. Preferably, the undersurfaces 63 of the lugs 61 are rounded to facilitate caming of the lugs 61 over the chamfered edge 47 of the stiffener ring 25. The thickness of the tangs 45 between the lugs 61 and the annulus 43 allows for outward deformation of the tangs 45 as the lugs 61 are camed over the chamfered edge 47.

The fabric covering 15 is formed of fabric selected for lifetime durability as well as compatibility with blood and heart tissue. A woven or knitted fabric provides porosity for ingrowth of heart tissue, and a preferred material for the fabric member is Dacron (polyethylene terephthalate) knit fabric. The length of the tubular fabric member is sufficient to fully surround the retainer ring 33, shock absorbing member 26 and cushioning member 28.

The cushioning member 28 is formed of a resiliently deformable rubber-like material which is biocompatible, preferably silicone. The cushioning member 28 has a semi-elliptical cross section. Two annular grooves 32 and 24 are formed in the underside of the cushioning member 28. These grooves 32 and 24 are sufficiently dimensioned and positioned to increase the flexibility of the member 28. This underside is further provided with a third annular groove 18, which is positioned and dimensioned to receive the curved section 41 of the retainer ring 33. The cushioning ring 28 allows easy penetration by suturing needles.

Figure 5:
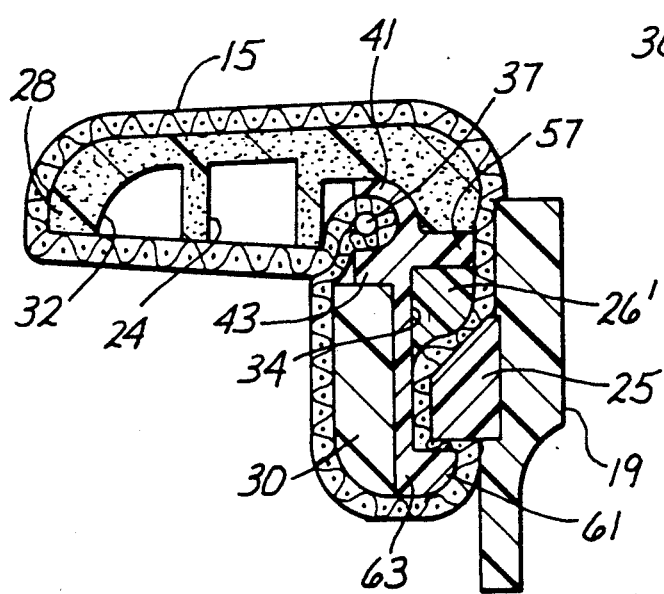
FIG. 5 is a cross-sectional view of a sewing ring and valve body of an embodiment of the invention.

The shock absorbing member 26 is also formed from a resiliently deformable rubber-like material. This material may either be a solid piece of material, e.g. silicone ring, or be formed from a paste-like extrusion of suitable material as seen in FIG. 5 at 26'. The shock absorbing member 26 is positioned against the overhang 57. When the retainer ring 33 is snapped upon the stiffener ring 25, the shock absorbing member 26 will be forced between the two rings 33 and 25. This not only provides for a cushioning effect, but provides for a positive retention of the retainer ring 33 to the stiffener ring 25. In the illustrated embodiment, the orifice ring 19 rotates in the sewing ring assembly 13, with the shock absorbing member 26 providing calibrated torque for this rotation.

The assembly of the sewing ring assembly 13 involves positioning the circular section 41 of the retainer ring 33 in the annular groove 18, placing the shock absorbing member 26 against the overhang 57 and then wrapping these members with the fabric covering 15. The respective fabric ends 35a and 35b are then sewn with the suture 37, which is fitted in the circular section 41. The entire sewing ring assembly 13 is then fitted to the orifice ring 19 by snapping the cloth covered retainer ring 33 over the stiffener ring 25. This is performed by camming the lugs 61 across the chamfered surface 47 of the stiffened ring 25. The shock absorbing member 26 enhances the fit of the retainer ring 33 to the stiffener ring 25, as well as providing a cushion effect between these two ring members.

The sewing ring assembly 13 of the invention may also include a spacing member 30. This spacing member 30 is typically used when the sewing ring assembly 13 is being constructed for a larger size sewing ring for the mechanical heart valve. Generally, thirty-one to thirty-three millimeter heart valves require a larger dimensioned sewing ring assembly 13. In these situations the spacing member 30 is fitted against the retainer ring 33 at the opposite side of the annular groove 34. The spacing member 30 is also preferably formed from a rubber-like material, i.e. silicone.

An alternative embodiment to the invention is seen in FIG. 5. As illustrated, the shock absorbing member 26' is formed from a layer of silicone gel which is disposed along the overhang 57 during the assembly of the sewing ring assembly 13. This silicone gel provides the same type of cushioning and enhancing fit as does the silicone 0-Ring described above.

While the preferred embodiments have been described, various modifications and substitutions may be made thereto without departing from the scope of the invention. Accordingly, it is to be understood that the invention has been described by way of illustration and not limitation.

What is claimed is:
1. A heart valve comprising:
a substantially cylindrically shaped valve body formed from an inelastic, deformable material having a substantially circular first opening therethrough, an exterior wall, and an interior wall surrounding said first opening, said interior wall defining an annular ledge;
one or more occluders pivotally mounted to said interior wall within said first opening, said occluders being dimensioned to engage said annular ledge which restricts further pivoting action of said occluders;
stiffening member formed from a substantially nonresilient material fitted about said valve body exterior wall; and
a sewing ring formed about said valve body comprising:
a rigid retainer means formed to be held about said valve body exterior surface for holding said sewing ring in position, said retainer means being positioned adjacent to said stiffening member;
shock absorbing means formed from a rubber-like material disposed between said stiffening member and said retainer means for absorbing and cushioning impact between said member and said retainer means;
cushioning member formed from a rubber-like material which extends out from said exterior surface of said valve body; and
a length of fabric surrounding said sewing ring.
2. The heart valve of claim 1 wherein said exterior wall of said valve body is formed with a groove into which said stiffening member fits.
3. The heart valve of claim 1 wherein said shock absorbing means is an O-Ring positioned between said retainer means and said stiffening member.
4. The heart valve of claim 1 wherein said shock absorbing means is silicone gel positioned between said retainer means and stiffening member.
5. The heart valve of claim 3 wherein said O-ring is formed from silicone.
6. The heart valve of claim 5 wherein said valve body is formed from pyrolytic carbon.
7. The heart valve of claim 6 wherein said stiffening member is an annular shaped body.
8. The heart valve of claim 7 wherein said rigid retainer means is an annular shaped body formed to snappily engage said stiffening member.
9. The heart valve of claim wherein said stiffening member includes a chamfered surface across which said rigid retainer means is cammed.
10. The heart valve of claim 9 wherein said rigid retainer means is formed with an extension defining an annular groove for receiving said stiffening member, said extension including a portion which engages and cams across said stiffening member chamfered surface to snappily engage said stiffener means.

* * * * *